(12) United States Patent
Svestka

(10) Patent No.: US 12,427,008 B2
(45) Date of Patent: Sep. 30, 2025

(54) FULL COVERAGE ABDOMINAL ANATOMIC HERNIA MESH

(71) Applicant: Michael Grant Svestka, Great Falls, VA (US)

(72) Inventor: Michael Grant Svestka, Great Falls, VA (US)

( * ) Notice: Subject to any disclaimer, the term of this patent is extended or adjusted under 35 U.S.C. 154(b) by 122 days.

(21) Appl. No.: 18/403,540

(22) Filed: Jan. 3, 2024

(65) Prior Publication Data

US 2024/0285385 A1    Aug. 29, 2024

Related U.S. Application Data

(60) Provisional application No. 63/486,852, filed on Feb. 24, 2023.

(51) Int. Cl.
*A61F 2/00* (2006.01)

(52) U.S. Cl.
CPC .................. *A61F 2/0063* (2013.01)

(58) Field of Classification Search
CPC ............ A61F 2002/0068; A61F 2/0077; A61F 2/0063; A61F 2/0045; A61F 2230/0045
See application file for complete search history.

(56) References Cited

U.S. PATENT DOCUMENTS

| | | | | |
|---|---|---|---|---|
| 6,391,060 B1* | 5/2002 | Ory | ...................... | A61F 2/0063 606/151 |
| 6,652,595 B1* | 11/2003 | Nicolo | .................. | A61F 2/0063 623/23.72 |
| 2008/0113001 A1* | 5/2008 | Herweck | .................. | A61L 31/14 424/445 |
| 2009/0187197 A1* | 7/2009 | Roeber | .................. | D04B 21/12 606/151 |
| 2010/0312043 A1* | 12/2010 | Goddard | ............... | A61F 2/0045 600/30 |
| 2021/0244521 A1* | 8/2021 | Towfigh | ................ | A61F 2/0063 |

* cited by examiner

*Primary Examiner* — Mohamed G Gabr

(57) ABSTRACT

A full coverage abdominal anatomic hernia mesh includes an upper mesh section, a lower mesh section, a lateral edge, and a horizontal axis. The lateral edge includes a first inflection point, an upper concave edge, a second inflection point, a lower-left concave edge, a third inflection point, a lower convex edge, a fourth inflection point, and a lower-right concave edge to define the preferred shape. The upper mesh section is adjacently connected to the lower mesh section along the horizontal axis. The lateral edge is perimetrically positioned around the upper mesh section and the lower mesh section. The upper concave edge is extended from the first inflection point to the second inflection point and adjacent to the upper mesh section. The lower-left concave edge, the third inflection point, the lower convex edge, the fourth inflection point, and the lower-right concave edge are positioned adjacent to the lower mesh section.

18 Claims, 5 Drawing Sheets

FULL COVERAGE ABDOMINAL ANATOMIC HERNIA MESH

FIELD OF THE INVENTION

The present invention relates generally to hernia repair. More specifically, the present invention is an individual prosthetic mesh that is anatomically configured to provide reinforcement to not only the midline and lateral abdomen, but also to the bilateral inguinal regions during abdominal wall reconstruction with the intention of treating all abdominal wall hernias.

BACKGROUND OF THE INVENTION

A hernia is characterized by a defect in the abdominal wall through which an organ, intestine, or fatty tissue can protrude. Hernias are often caused by a combination of tissue weakness, trauma, or prior incisions, and pose medical risk in that intestines can become trapped or incarcerated in these defects and lead to bowel compromise or death. According to the U.S. Food & Drug Administration, more than one million hernia repairs are performed each year in the U.S. Landmark studies from 2000 and 2004 demonstrated that the use of mesh prevents the risk of hernia recurrence by more than two times, and thus has become the standard of care. A hernia mesh is a type of medical prosthetic typically made from synthetic or biologic materials and is used to strengthen the hernia repair and reduce the rate of recurrence.

The use of hernia mesh for prosthetic reinforcement of abdominal hernia defects has been a well-established practice for over 50 years. Commercially-available mesh products are typically manufactured using polypropylene, polyester, or ePTFE polymers and are available in a number of sizes ranging from 2-3 centimeters (cm) to 50×50 cm sheets.

Hernia repair is generally approached in a stepwise fashion whereby the extent of the repair is dictated by the size of the hernia. Smaller hernias, therefore, require smaller mesh products while larger hernias require larger meshes. While smaller hernia defects are amenable to local repairs, as these defects recur and enlarge, reconstructive techniques utilizing muscle flaps developed out of abdominal wall tissue planes are required. Abdominal wall reconstruction is a category of hernia repair that encompasses a variety of surgical techniques used to fully reconstruct the abdominal wall and is indicated for very large hernia defects, or circumstances where numerous or recurrent hernia defects require definitive repair.

For very large hernia defects, reconstructive techniques called "component separations" are used to separate the layers of the abdominal wall musculature. One such technique, known as transversus abdominis release, allows for coverage of the entire peritoneal cavity with reinforcing mesh. Here, the tissue planes between muscle and fascia are developed and bilateral myofascial flaps are advanced towards the midline to close the visceral space. This allows for an extraperitoneal mesh to be placed between myofascial layers for reinforcement, placing the mesh outside of the peritoneal cavity (organ space) and between the abdominal wall muscles. These techniques of abdominal wall reconstruction generally use very large sheets of mesh to reinforce midline, off-midline, and lateral hernia defects of the abdominal wall.

During abdominal wall reconstruction, the myofascial advancement flaps extend from the xiphoid to the pubic symphysis in the craniocaudal dimension, and bilaterally towards the retroperitoneum. Currently-available mesh products do not encompass the full breadth of dissection during this procedure and fail to support the entirety of the abdominal wall. More specifically, currently-available commercial mesh configurations allow for large sheets of diamond-shaped mesh to be placed in the cavity for reinforcement. These configurations, however, lack anatomic specificity and fail to reinforce the bilateral inguinal spaces (groins) which are necessarily developed during flap dissection. This is important as many patients undergoing abdominal wall reconstruction concurrently have large inguinal hernias at the time of operation. Current mesh products require the use of a second mesh to be placed, overlapping the central mesh into the groins.

An objective of the present invention is to provide a solution to the aforementioned problems. More specifically, it is an aim of the present invention to provide a single mesh prosthetic that covers the full extent of the abdominal wall. The present invention is a total abdominal mesh which is anatomically-configured to provide reinforcement to not only the midline and lateral abdomen, but also to the bilateral inguinal regions during abdominal wall reconstruction. Reinforcement of the bilateral inguinal regions is particularly important to prevent hernia recurrence, as well as to treat concurrent inguinal hernias during abdominal wall reconstruction for midline and lateral hernias.

SUMMARY OF THE INVENTION

The present invention is a total abdominal anatomic hernia mesh designed to cover the full extent of the abdominal wall during abdominal wall reconstruction. The present invention is anatomically configured to provide reinforcement to not only the midline and lateral abdomen, but also to the bilateral inguinal regions as well. The present invention comprises a single sheet of hernia mesh that is uniquely shaped to cover all regions described above. More specifically, the upper section comprises a convex-shaped top and a pair of upper flaps, the plurality of which covers the abdominal region. The lower section (base) comprises a concave-shaped bottom and a pair of lower flaps, the plurality of which covers the bilateral inguinal regions. Together, the upper section and the base provide full coverage of the abdominal wall during abdominal wall reconstruction.

DETAIL DESCRIPTIONS OF THE INVENTION

All illustrations of the drawings are for the purpose of describing selected versions of the present invention and are not intended to limit the scope of the present invention.

Figure 3:
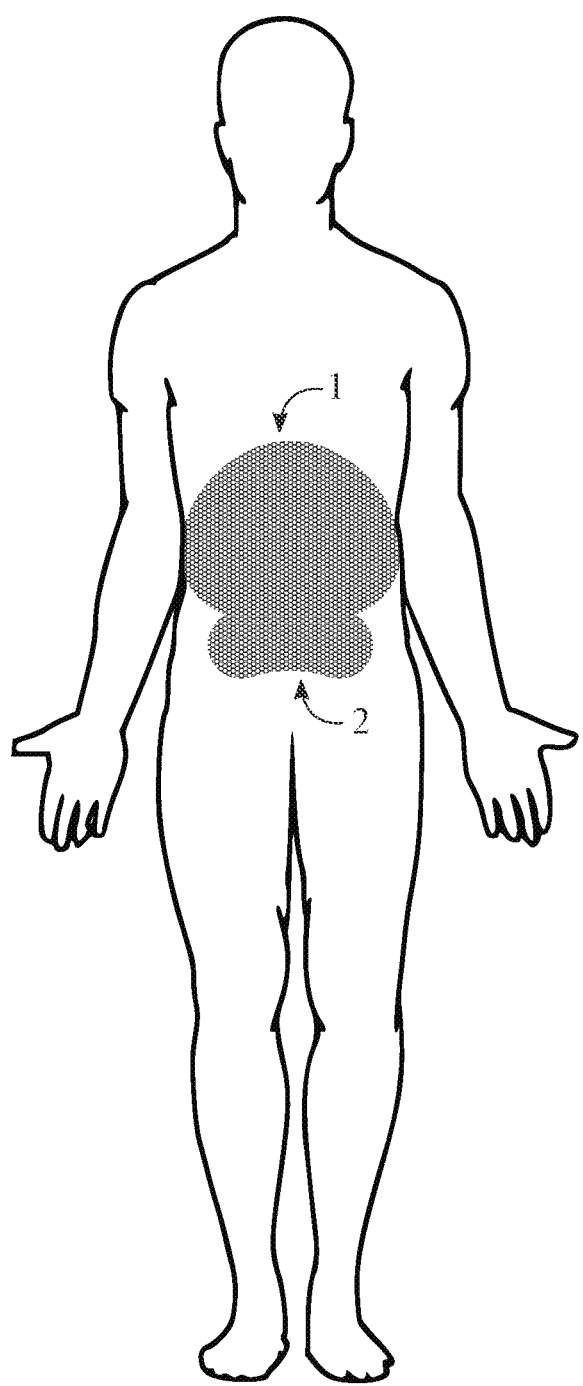
FIG. 3 is a front elevational view of the present invention, showing the placement of the present invention in relation to a human body.

The present invention is a full coverage abdominal anatomic hernia mesh. It is an aim of the present invention to provide a mesh prosthetic that covers the full extent of the abdominal wall, as seen in FIG. 3. More specifically, the present invention is anatomically-configured to provide reinforcement to not only the midline and lateral abdomen, but also to the bilateral inguinal regions during abdominal wall reconstruction. With regards to shape, the present invention is a singular prosthetic that is uniquely shaped to reinforce four types of hernia defects including midline, off-midline, lateral, and inguinal hernias. Although the shape of the present invention is defined hereafter, the size of the present invention is not limited. In other words, the present invention can be produced in various sizes to accommodate patient anatomy. Similarly, the material of the present invention is not limited, and can be made of any type of medical-grade material based on design, user, manufacturing requirements, and/or medical requirements.

As shown in FIG. 1-4, the present invention comprises an upper mesh section 1, a lower mesh section 2, a lateral edge 3, and a horizontal axis 12. More specifically, the upper mesh section 1 is adjacently connected to the lower mesh section 2 along the horizontal axis 12, forming a single hernia mesh piece. The lateral edge 3 is perimetrically positioned around the upper mesh section 1 and the lower mesh section 2 thus defining the outer edge of the present invention. In this arrangement, the upper mesh section 1 is anatomically shaped to reinforce the abdominal core (midline, off-midline, and lateral abdomen). The lower mesh section 2 that is centered below the upper mesh section 1 is anatomically shaped to reinforce the bilateral inguinal regions. The overall shape of the present invention is able to cover the full extent of the abdominal wall and treats all hernia defects. As a result, the present invention is able to prevent overlapping of multiple hernia meshes method that is currently conducted within the medical industry.

Figure 1:
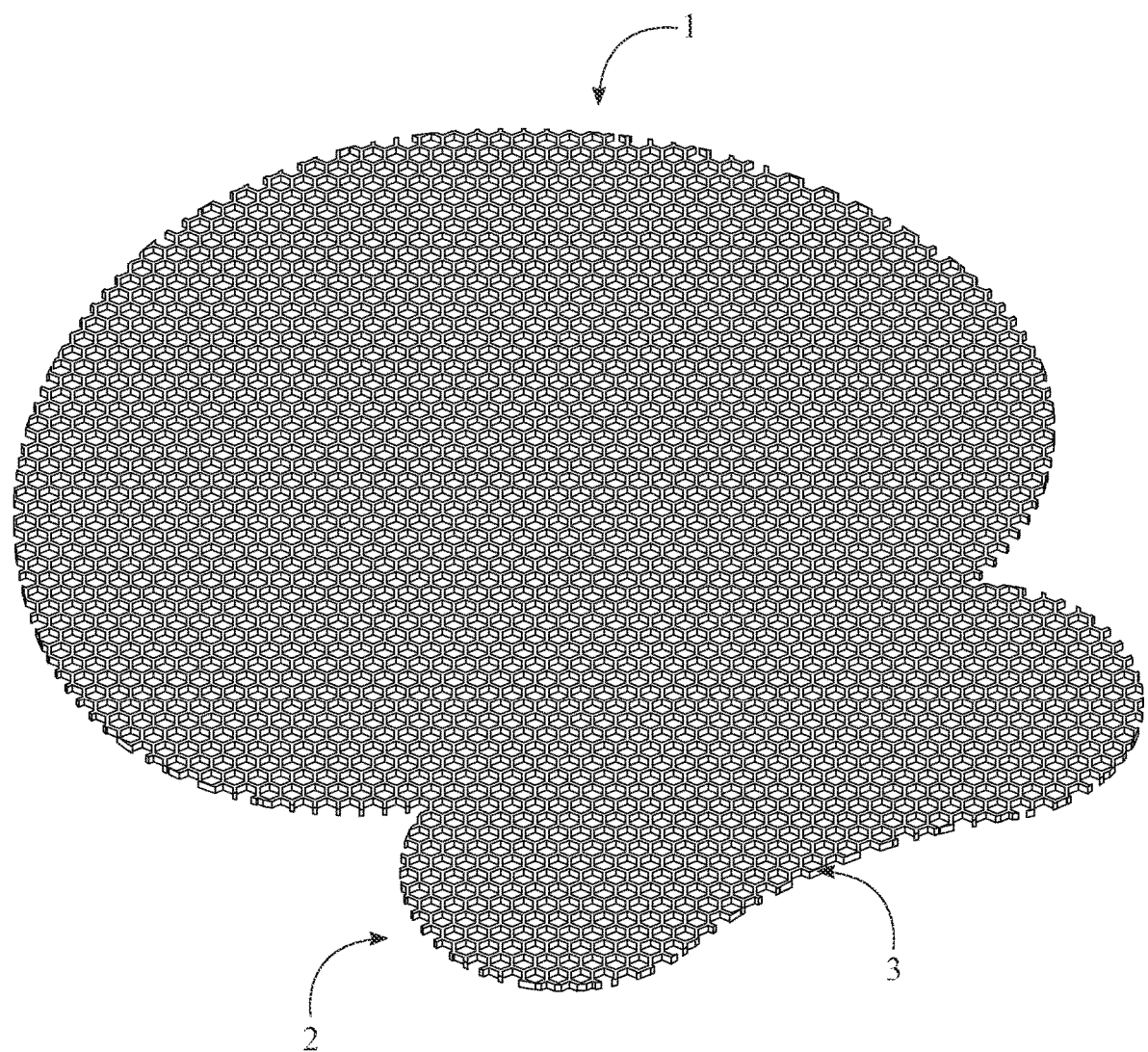
FIG. 1 is a perspective view of the present invention.
Figure 2:
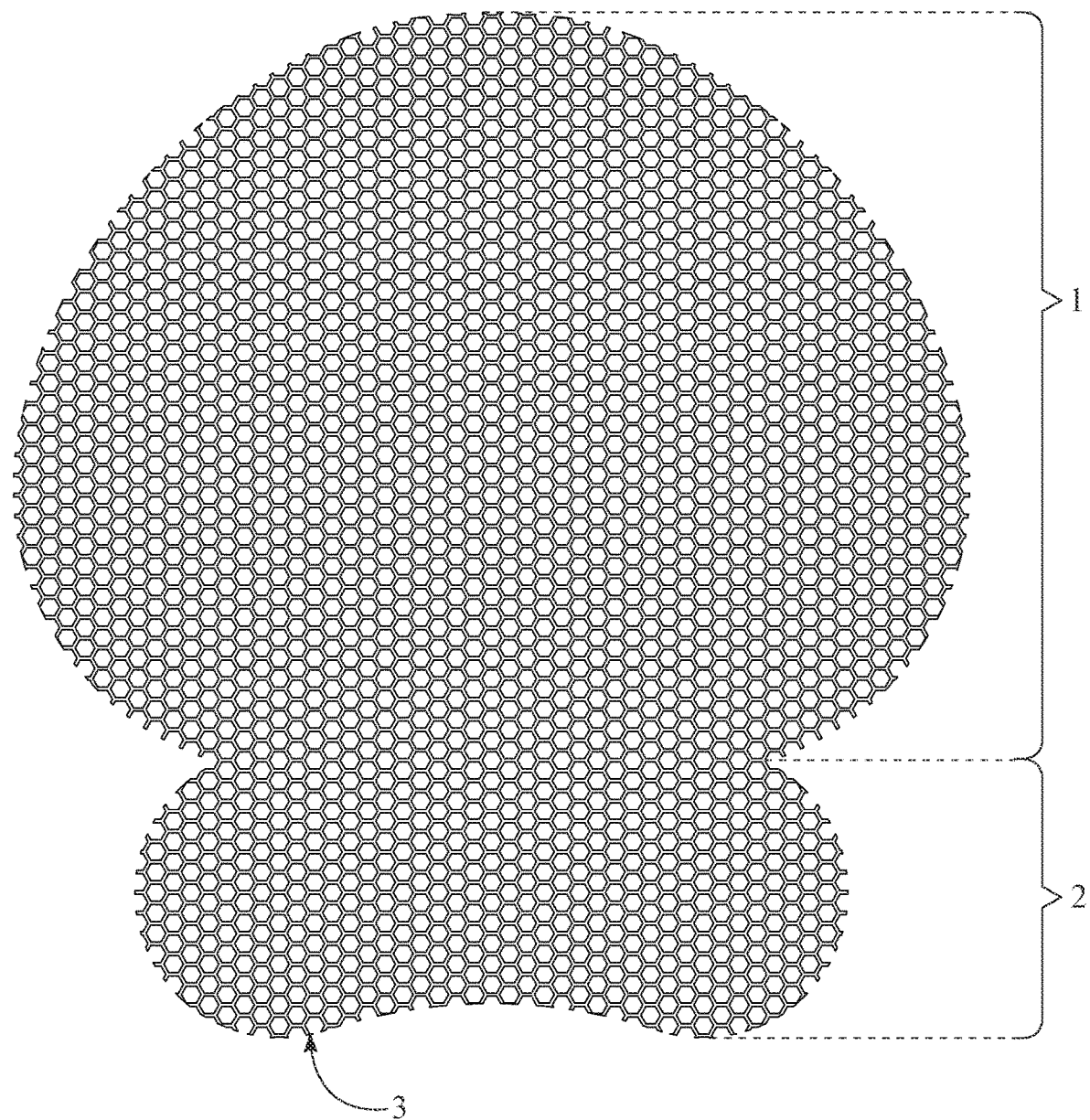
FIG. 2 is a front elevational view of the present invention.
Figure 4:
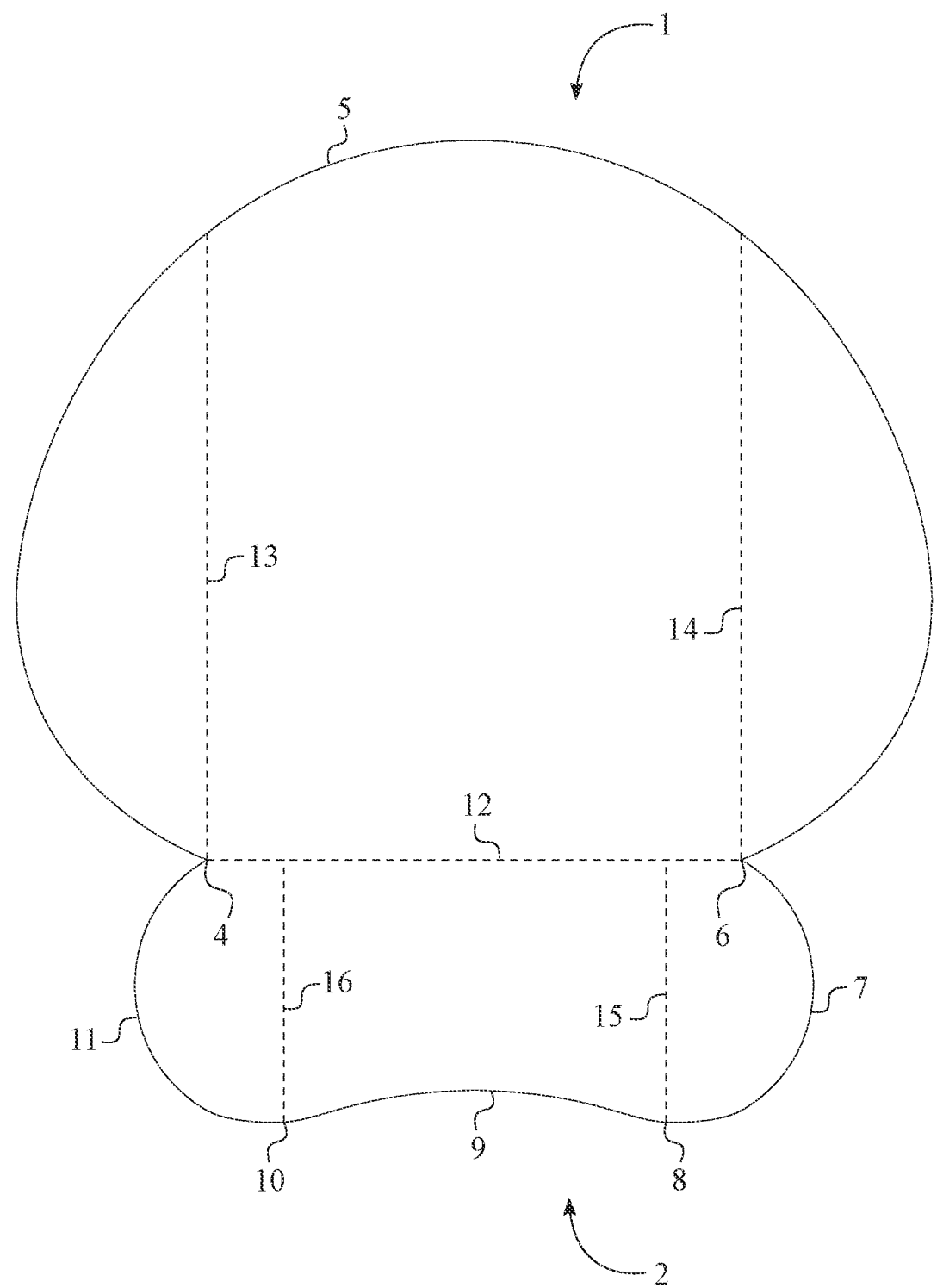
FIG. 4 is a schematic view of the present invention, showing the first inflection point, the second inflection point, the third inflection point, the fourth inflection point, the upper concave edge, the lower-left concave edge, the lower convex edge, and the lower-right concave edge, and wherein the dash lines illustrates the horizontal axis, the first vertical axis, the second vertical axis, the third vertical axis, and the fourth vertical axis.

As shown in FIG. 2 and FIG. 4, the lateral edge 3 comprises a first inflection point 4, an upper concave edge 5, a second inflection point 6, a lower-left concave edge 7, a third inflection point 8, a lower convex edge 9, a fourth inflection point 10, and a lower-right concave edge 11 so that the preferred shaped of the present invention can be explained. More specifically, the horizontal axis 12 is positioned in between the upper mesh section 1 and the lower mesh section 2 and linearly extended from the first inflection point 4 to the second inflection point 6. The first inflection point 4 and the second inflection point 6 are oppositely positioned of each other about the horizontal axis 12 and function as terminal ends of the horizontal axis 12. In other words, the first inflection point 4, the horizontal axis 12, and the second inflection point 6 separate the upper mesh section 1 from the lower mesh section 2. when the present invention is utilized to treat abdominal wall hernia, the first inflection point 4 and the second inflection point 6 are positioned adjacent to a natural indentation in the pelvic bones so that the positioning of the present invention can be optimized during the abdominal wall reconstruction.

As shown in FIG. 2 and FIG. 4, the upper concave edge 5 is positioned adjacent to the upper mesh section 1 as the upper concave edge 5 is extended from the first inflection point 4 to the second inflection point 6. In other words, the specific area defined by the first inflection point 4, the upper concave edge 5, the second inflection point 6, and the horizontal axis 12 is identified as the preferred shape of the upper mesh section 1.

As shown in FIG. 2 and FIG. 4, the lower-left concave edge 7, the third inflection point 8, the lower convex edge 9, the fourth inflection point 10, and the lower-right concave edge 11 are positioned adjacent to the lower mesh section 2. In other words, the specific area defined by the first inflection point 4, the horizontal axis 12, the second inflection point 6, the lower-left concave edge 7, the third inflection point 8, the lower convex edge 9, the fourth inflection point 10, and the lower-right concave edge 11 is identified as the preferred shape of the lower mesh section 2. More specifically, the lower convex edge 9 is symmetrically positioned in between the first inflection point 4 and the second inflection point 6. The third inflection point 8 and the fourth inflection point 10 are oppositely positioned of each other about the lower convex edge 9 thus functioning as the terminal ends of the lower convex edge 9. The lower-left concave edge 7 is extended from the second inflection point 6 to the third inflection point 8 so that a left end of the lower mesh section 2 can be configured. The lower-right concave edge 11 is extended from the first inflection point 4 to the fourth inflection point 10 so that a right end of the lower mesh section 2 can be configured.

As shown in FIG. 2 and FIG. 4, the present invention further comprises a first vertical axis 13 and a second vertical axis 14 so that the upper mesh section 1 can be separated into three functional regions. The first vertical axis 13 is perpendicularly positioned to the horizontal axis 12 and linearly extended from the first inflection point 4 to the upper concave edge 5. The second vertical axis 14 is perpendicularly positioned to the horizontal axis 12 and linearly extended from the second inflection point 6 to the upper concave edge 5. In other words, the first vertical axis 13 and the second vertical axis 14 are positioned offset of each other and extended into the upper concave edge 5 from the terminal ends of the horizontal axis 12.

Figure 5:
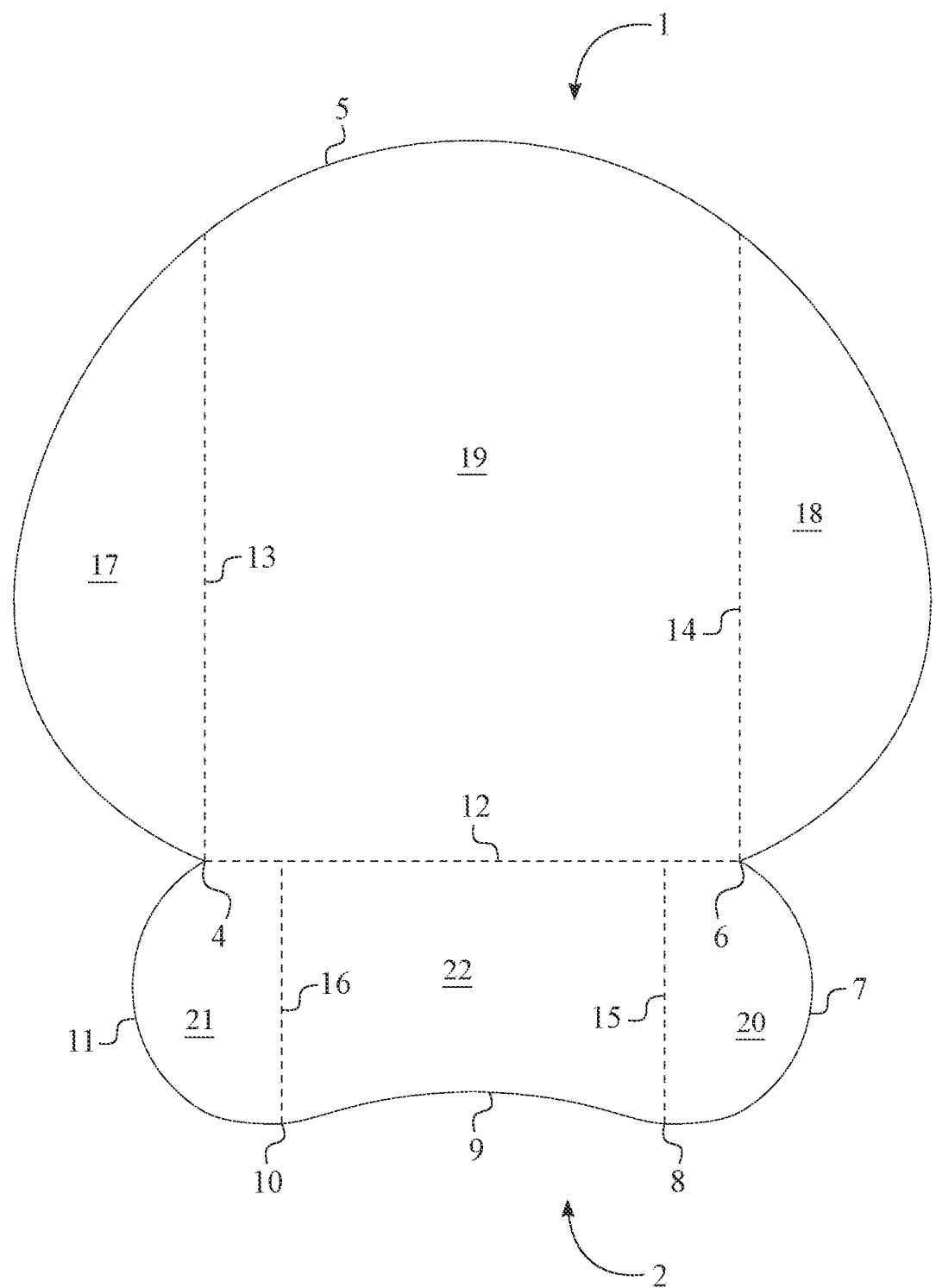
FIG. 5 is a schematic view of the present invention, showing the right subcostal margin and right flank region, the left subcostal margin and left flank region, the epigastric and central abdomen region, the left inguinal region, the right inguinal region, and the suprapubic and retzius space region.

As shown in FIG. 4-5, the present invention further comprises a right subcostal margin and right flank region 17. The right subcostal margin and right flank region 17 is positioned within the upper mesh section 1 so that the present invention can extend over the abdominal wall and into the right rib cage to treat hernia repair and to prevent potential hernia spaces. More specifically, the right subcostal margin and right flank region 17 is delineated by the first inflection point 4, the upper concave edge 5, and the first vertical axis 13 to fully cover the abdominal wall and the right rib cage.

As shown in FIG. 4-5, the present invention further comprises a left subcostal margin and left flank region 18. The left subcostal margin and left flank region 18 is positioned within the upper mesh section 1 so that the present invention can extend over the abdominal wall and into the left rib cage to treat hernia repair and to prevent potential hernia spaces. More specifically, the left subcostal margin and left flank region 18 is delineated by the second inflection point 6, the upper concave edge 5, and the second vertical axis 14 to fully cover the abdominal wall and the left rib cage.

As shown in FIG. 4-5, the present invention further comprises an epigastric and central abdomen region 19. The epigastric and central abdomen region 19 is positioned within the upper mesh section 1 so that the present invention can extend over the abdominal wall to treat hernia repair and to prevent potential hernia spaces. More specifically, the epigastric and central abdomen region 19 is delineated by the first vertical axis 13, the upper concave edge 5, the second vertical axis 14, and the horizontal axis 12 to fully cover the abdominal wall in between the right subcostal margin and right flank region 17 and the left subcostal margin and left flank region 18.

As shown in FIG. 2 and FIG. 4, the present invention further comprises a third vertical axis 15 and a fourth vertical axis 16 so that the lower mesh section 2 can be separated into three functional regions. The third vertical axis 15 is perpendicularly positioned to the horizontal axis 12 and positioned adjacent to the second inflection point 6. The third vertical axis 15 is linearly extended from the horizontal axis 12 to the third inflection point 8 as the third vertical axis 15 is positioned adjacent and oppositely extended from the second vertical axis 14. The fourth vertical axis 16 is perpendicularly positioned to the horizontal axis 12 and positioned adjacent to the first inflection point 4. The fourth vertical axis 16 is linearly extended from the horizontal axis 12 to the fourth inflection point 10 as the fourth vertical axis 16 is positioned adjacent and oppositely extended from the first vertical axis 13.

As shown in FIG. 4-5, the present invention further comprises a left inguinal region 20. The left inguinal region 20 is positioned within the lower mesh section 2 so that the present invention can extend over the left inguinal area of the abdomen to treat hernia repair and to prevent potential hernia spaces. More specifically, the left inguinal region 20 is delineated by the second inflection point 6, the lower-left concave edge 7, the third inflection point 8, the third vertical axis 15, and the horizontal axis 12 to fully cover the left inguinal area of the abdomen.

As shown in FIG. 4-5, the present invention further comprises a right inguinal region 21. The right inguinal region 21 is positioned within the lower mesh section 2 so that the present invention can extend over the right inguinal area of the abdomen to treat hernia repair and to prevent potential hernia spaces. More specifically, the right inguinal region 21 is delineated by the first inflection point 4, the lower-right concave edge 11, the fourth inflection point 10, the fourth vertical axis 16, and the horizontal axis 12 to fully cover the right inguinal area of the abdomen.

As shown in FIG. 4-5, the present invention further comprises a suprapubic and retzius space region 22. The suprapubic and retzius space region 22 is positioned within the lower mesh section 2 so that the present invention can position below the bladder and rest adjacent to the copper ligament. More specifically, the suprapubic and retzius space region 22 is delineated by the third inflection point 8, the lower convex edge 9, the fourth inflection point 10, the fourth vertical axis 16, the horizontal axis 12, and the third vertical axis 15 to fully cover the hypogastric area of the abdomen.

Although the invention has been explained in relation to its preferred embodiment, it is to be understood that many other possible modifications and variations can be made without departing from the spirit and scope of the invention as hereinafter claimed.

What is claimed is:

1. A full coverage abdominal anatomic hernia mesh comprising:
    an upper mesh section;
    a lower mesh section;
    a lateral edge;
    a horizontal axis;
    the lateral edge comprising a first inflection point, an upper concave edge, a second inflection point, a lower-left concave edge, a third inflection point, a lower convex edge, a fourth inflection point, and a lower-right concave edge;
    the upper mesh section being adjacently connected to the lower mesh section along the horizontal axis;
    the lateral edge being perimetrically positioned around the upper mesh section and the lower mesh section;
    the first inflection point and the second inflection point being oppositely positioned of each other about the horizontal axis;
    the upper concave edge being positioned adjacent to the upper mesh section;
    the upper concave edge being extended from the first inflection point to the second inflection point;
    the lower-left concave edge, the third inflection point, the lower convex edge, the fourth inflection point, and the lower-right concave edge being positioned adjacent to the lower mesh section;
    the lower convex edge being symmetrically positioned in between the first inflection point and the second inflection point;
    the third inflection point and the fourth inflection point being oppositely positioned of each other about the lower convex edge;
    the lower-left concave edge being extended from the second inflection point to the third inflection point; and
    the lower-right concave edge being extended from the first inflection point to the fourth inflection point.

2. The full coverage abdominal anatomic hernia mesh as claimed in claim 1 comprising:
    the horizontal axis being positioned in between the upper mesh section and the lower mesh section; and
    the horizontal axis being linearly extended from the first inflection point to the second inflection point.

3. The full coverage abdominal anatomic hernia mesh as claimed in claim 1 comprising:
    a first vertical axis;
    a second vertical axis;
    the first vertical axis being perpendicularly positioned to the horizontal axis;
    the first vertical axis being linearly extended from the first inflection point to the upper concave edge;
    the second vertical axis being perpendicularly positioned to the horizontal axis; and
    the second vertical axis being linearly extended from the second inflection point to the upper concave edge.

4. The full coverage abdominal anatomic hernia mesh as claimed in claim 3 comprising:
    a right subcostal margin and right flank region;
    the right subcostal margin and right flank region being positioned within the upper mesh section; and
    the right subcostal margin and right flank region being delineated by the first inflection point, the upper concave edge, and the first vertical axis.

5. The full coverage abdominal anatomic hernia mesh as claimed in claim 3 comprising:
    a left subcostal margin and left flank region;
    the left subcostal margin and left flank region being positioned within the upper mesh section; and
    the left subcostal margin and left flank region being delineated by the second inflection point, the upper concave edge, and the second vertical axis.

6. The full coverage abdominal anatomic hernia mesh as claimed in claim 3 comprising:
    an epigastric and central abdomen region;
    the epigastric and central abdomen region being positioned within the upper mesh section; and the epigastric and central abdomen region being delineated by the first vertical axis, the upper concave edge, the second vertical axis, and the horizontal axis.

7. The full coverage abdominal anatomic hernia mesh as claimed in claim 1 comprising:
a third vertical axis;
a fourth vertical axis;
the third vertical axis being perpendicularly positioned to the horizontal axis;
the third vertical axis being positioned adjacent to the second inflection point;
the third vertical axis being linearly extended from the horizontal axis to the third inflection point;
the fourth vertical axis being perpendicularly positioned to the horizontal axis;
the fourth vertical axis being positioned adjacent to the first inflection point; and
the fourth vertical axis being linearly extended from the horizontal axis to the fourth inflection point.

8. The full coverage abdominal anatomic hernia mesh as claimed in claim 7 comprising:
a left inguinal region;
the left inguinal region being positioned within the lower mesh section; and
the left inguinal region being delineated by the second inflection point, the lower-left concave edge, the third inflection point, the third vertical axis, and the horizontal axis.

9. The full coverage abdominal anatomic hernia mesh as claimed in claim 7 comprising:
a right inguinal region;
the right inguinal region being positioned within the lower mesh section; and
the right inguinal region being delineated by the first inflection point, the lower-right concave edge, the fourth inflection point, the fourth vertical axis, and the horizontal axis.

10. The full coverage abdominal anatomic hernia mesh as claimed in claim 7 comprising:
a suprapubic and retzius space region;
the suprapubic and retzius space region being positioned within the lower mesh section; and
the suprapubic and retzius space region being delineated by the third inflection point, the lower convex edge, the fourth inflection point, the fourth vertical axis, the horizontal axis, and the third vertical axis.

11. A full coverage abdominal anatomic hernia mesh comprising:
an upper mesh section;
a lower mesh section;
a lateral edge;
a horizontal axis;
a first vertical axis;
a second vertical axis;
a third vertical axis;
a fourth vertical axis;
the lateral edge comprising a first inflection point, an upper concave edge, a second inflection point, a lower-left concave edge, a third inflection point, a lower convex edge, a fourth inflection point, and a lower-right concave edge;
the upper mesh section being adjacently connected to the lower mesh section along the horizontal axis;
the lateral edge being perimetrically positioned around the upper mesh section and the lower mesh section;
the first inflection point and the second inflection point being oppositely positioned of each other about the horizontal axis;
the upper concave edge being positioned adjacent to the upper mesh section;
the upper concave edge being extended from the first inflection point to the second inflection point;
the lower-left concave edge, the third inflection point, the lower convex edge, the fourth inflection point, and the lower-right concave edge being positioned adjacent to the lower mesh section;
the lower convex edge being symmetrically positioned in between the first inflection point and the second inflection point;
the third inflection point and the fourth inflection point being oppositely positioned of each other about the lower convex edge;
the lower-left concave edge being extended from the second inflection point to the third inflection point;
the lower-right concave edge being extended from the first inflection point to the fourth inflection point;
the first vertical axis being perpendicularly positioned to the horizontal axis;
the first vertical axis being linearly extended from the first inflection point to the upper concave edge;
the second vertical axis being perpendicularly positioned to the horizontal axis;
the second vertical axis being linearly extended from the second inflection point to the upper concave edge;
the third vertical axis being perpendicularly positioned to the horizontal axis;
the third vertical axis being positioned adjacent to the second inflection point;
the third vertical axis being linearly extended from the horizontal axis to the third inflection point;
the fourth vertical axis being perpendicularly positioned to the horizontal axis;
the fourth vertical axis being positioned adjacent to the first inflection point; and
the fourth vertical axis being linearly extended from the horizontal axis to the fourth inflection point.

12. The full coverage abdominal anatomic hernia mesh as claimed in claim 11 comprising:
the horizontal axis being positioned in between the upper mesh section and the lower mesh section; and
the horizontal axis being linearly extended from the first inflection point to the second inflection point.

13. The full coverage abdominal anatomic hernia mesh as claimed in claim 11 comprising:
a right subcostal margin and right flank region;
the right subcostal margin and right flank region being positioned within the upper mesh section; and
the right subcostal margin and right flank region being delineated by the first inflection point, the upper concave edge, and the first vertical axis.

14. The full coverage abdominal anatomic hernia mesh as claimed in claim 11 comprising:
a left subcostal margin and left flank region;
the left subcostal margin and left flank region being positioned within the upper mesh section; and
the left subcostal margin and left flank region being delineated by the second inflection point, the upper concave edge, and the second vertical axis.

15. The full coverage abdominal anatomic hernia mesh as claimed in claim 11 comprising:
an epigastric and central abdomen region;

the epigastric and central abdomen region being positioned within the upper mesh section; and the epigastric and central abdomen region being delineated by the first vertical axis, the upper concave edge, the second vertical axis, and the horizontal axis.

16. The full coverage abdominal anatomic hernia mesh as claimed in claim 11 comprising:

a left inguinal region;

the left inguinal region being positioned within the lower mesh section; and the left inguinal region being delineated by the second inflection point, the lower-left concave edge, the third inflection point, the third vertical axis, and the horizontal axis.

17. The full coverage abdominal anatomic hernia mesh as claimed in claim 11 comprising:

a right inguinal region;

the right inguinal region being positioned within the lower mesh section; and the right inguinal region being delineated by the first inflection point, the lower-right concave edge, the fourth inflection point, the fourth vertical axis, and the horizontal axis.

18. The full coverage abdominal anatomic hernia mesh as claimed in claim 11 comprising:

a suprapubic and retzius space region;

the suprapubic and retzius space region being positioned within the lower mesh section; and the suprapubic and retzius space region being delineated by the third inflection point, the lower convex edge, the fourth inflection point, the fourth vertical axis, the horizontal axis, and the third vertical axis.

* * * * *